United States Patent
Jones et al.

(10) Patent No.: US 6,372,479 B1
(45) Date of Patent: Apr. 16, 2002

(54) FUSARIUM SPOROTRICHIOIDES STRAINS FOR PRODUCTION OF B-CAROTENE

(75) Inventors: James D. Jones, Chicago, IL (US); Thomas M. Hohn, Chapel Hill, NC (US); Timothy D. Leathers, Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/656,062

(22) Filed: Sep. 6, 2000

Related U.S. Application Data (62) Division of application No. 09/360,083, filed on Jul. 23, 1999, now Pat. No. 6,184,000.

(51) Int. Cl.⁷ .......................... C12N 1/15; C12N 15/80; C12N 1/21; C12P 1/02; C12P 21/06
(52) U.S. Cl. ............................. 435/252.3; 435/254.7; 435/41; 435/69.1; 435/471; 435/320.1; 536/23.1
(58) Field of Search .................... 435/67, 41, 320.1, 435/471, 254.7, 252.3, 69.1; 536/23.1

(56) References Cited

PUBLICATIONS

Jones, J. D., "Introduction and Expression of Isoprenoid Biosynthetic Pathways in *Fusarium Sporotrichioides*", Abstract, The Sixth Conference on the Genetics and Molecular Biology of Industrial Microorganisms (GMBIM), Oct. 20–24, 1996, Bloomington, IN, Unnumbered page.
Jones, J. D., "Metabolic Engineering of Triothecene–Producing *Fusarium*", Abstract, 1996 Annual Meeting of the Society for Industrial Microbiology, Research Triangle Park, NC Aug. 4–8, 1996, Unnumbered page.

*Primary Examiner*—David Guzo
*Assistant Examiner*—Gerald G. Leffers, Jr.
(74) *Attorney, Agent, or Firm*—M. Howard Silverstein; Randall E. Deck; John D. Fado (57) ABSTRACT

The instant invention is drawn towards transformed strains of *Fusarium sporotrichioides* effective for the production of B-carotene. The transformed strains comprise an expression cassette having four genes encoding, respectively, geranylgeranyl-pyrophosphate synthase, phytoene synthase, phytoene desaturase and lycopene cyclase (i.e. Tri5crtE, Tri5crtB, TriScrtI and CrtY). The transformed strains of *Fusarium sporotrichioides* of the instant invention produce B-carotene at levels of up to 3–4 milligrams per gram of fungus (dry weight).

1 Claim, 4 Drawing Sheets

FUSARIUM SPOROTRICHIOIDES STRAINS FOR PRODUCTION OF B-CAROTENE

This application is a division of application Ser. No. 09/360,083 now U.S. Pat. No. 6,184,000, filed Jul. 23, 1999 and incorporated by reference herein.

BACKGROUND OF THE INVENTION

1. Field of the Invention

The invention relates to a novel system and method for the sequential, directional cloning of multiple DNA sequences into a single vector.

2. Description of the Prior Art

The directional ligation of multiple DNA sequences within vectors is often hindered by the inability to force the orientation of subsequently ligated DNA fragments. This necessitates determination of fragment orientation following each ligation event to select recombinant plasmids with the inserts in the correct orientation (Potter, 1996, Biotechniques, 21:198–200). In addition, when attempting to clone a number of unrelated DNA fragments into a single host, the number of usable restriction sites declines rapidly, due to the presence of the sites in the insert DNA(s). Although it is sometimes possible to insert multiple genes into a single vector using a combination of available multicloning site (MCS) restriction sites (Jach et al., 1995, Plant Journal, 8:97–109; and Yamano et al., 1994, Biosci. Biotechnol. Biochem., 58:1112–1114), the process is often impractical. Moreover, the process is even more unreliable when attempting to directionally clone more than two genes into the vector.

SUMMARY OF THE INVENTION

We have now discovered a method which combines the use of polymerase chain reaction (PCR) or oligonucleotide linkers and restriction enzymes which cleave recognition site sequences that have internal degeneracy to allow the sequential, directional cloning of multiple DNA sequences into a DNA vector. In this invention, a plurality of unrelated DNA sequences may be directionally cloned within a single vector by adding onto the ends of the sequences, restriction sites with specific sequences which are cleaved by corresponding restriction endonucleases which recognize degenerate or variable recognition sites and which generate cohesive ends upon cleavage. The compatibility (or ability to anneal) of the cohesive ends on different DNA sequences is controlled by the choice of the nucleotide sequence within the recognition sequences of the restriction endonucleases, allowing the DNA sequences to be inserted or joined in any desired orientation.

Generally, a recipient DNA (such as a vector) is provided which has a first restriction site having a degenerate recognition sequence with a predetermined nucleotide sequence, and which upon digestion with its restriction enzyme generates cohesive ends. A DNA sequence to be inserted into the recipient DNA is provided with a different restriction site at each end, which also include degenerate recognition sequences. However, the nucleotide sequences of these degenerate recognition sequences are selected such that upon digestion, they give rise to first and second cohesive ends which are each complementary to only one of the cohesive ends on the recipient DNA. The first cohesive end on the insert DNA is only complementary to one cohesive end on the recipient DNA, while the second cohesive end on the insert DNA is only complementary to the other cohesive end on the recipient DNA. Thus, the directionality or desired orientation of the ligation of the inserted DNA to the recipient DNA or vector is ensured. Furthermore, by choosing such restriction sites which are the same (cleaved by the same restriction enzyme), or different (cleaved by different enzymes), the user may selectively predetermine if the functional restriction site is or is not regenerated after ligation. When the cohesive ends generated from two of the same restriction sites are annealed, the functional restriction site will be regenerated. In contrast, the cohesive ends generated from two different restriction sites, although complementary, will not regenerate a functional restriction site when annealed.

These restriction sites may be selectively incorporated onto the end(s) of any DNA sequence of interest using PCR by adding the restriction sites onto the termini of the 5' and/or 3' primers, or by adding linkers to the DNA sequence.

In this process, the first DNA sequence of interest may be inserted into the vector using either the process of this invention, or a variety of known techniques, including ligation into the vector at restriction sites generating blunt ends or cohesive ends, or a combination thereof. For instance, at least one end of the DNA sequence may be provided with a restriction site generating a cohesive end upon cleavage, which may then be inserted into the vector at any site which generates complementary cohesive ends.

To facilitate the ligation of additional DNA sequences, the first DNA sequence (further) includes one of the above-mentioned restriction sites having a degenerate recognition sequence adjacent (near) a selected end which also generates a cohesive end upon digestion with its corresponding restriction enzyme. This should be different from any other restriction sites present on the first DNA sequence, and should be unaffected by any initial restriction enzymes which may be used to insert the first sequence into the vector. This site should also be internal to any other different restriction sites used to insert the first DNA sequence into the vector to ensure that it is preserved.

The second DNA sequence of interest which is to be ligated adjacent to (upstream or downstream) from the first sequence is also provided with a restriction site adjacent to a selected first end that is different from the restriction site on the first sequence, and has a degenerate recognition sequence which, upon cleavage with its corresponding restriction enzyme, generates a cohesive end. The nucleotide sequences of the degenerate regions in these restriction sites (adjacent to the selected end of the first DNA sequence and the first end of the second DNA sequence) are selected such that the cohesive ends generated upon cleavage will be complementary to each other. If further DNA sequences are to be inserted into the vector adjacent to the second DNA sequence, the second DNA sequence should also include an additional restriction site adjacent to its opposite or second end which is essentially the same as the above-mentioned restriction site on the first end of the first DNA sequence. Moreover, because the restriction sites at the ends of the second DNA sequence generate asymmetric cohesive ends when cleaved, the directionality or orientation of the insertion into the vector may be readily controlled by selection of the restriction sites and the nucleotide sequences of their degenerate internal recognition regions.

Upon digestion of the restriction sites on the second DNA sequence and the restriction site on the selected end of the first DNA sequence (now contained within the recombinant plasmid) with their restriction enzymes, each of the ends on the cut vector will be compatible to only one of the ends on the second DNA sequence, ensuring directionality.

Specifically, the digestion of the restriction site on the first DNA sequence will generate overhangs on each end of the cut vector (one adjacent to the first DNA sequence and the other at the opposite end of the vector). The restriction site on the first end of the second DNA sequence will generate a cohesive end that is only complementary to the cohesive end adjacent to the first DNA sequence (i.e., at the selected end of the first DNA sequence), while the restriction site on the second end of the second DNA sequence will generate a cohesive end which is only complementary to the cohesive end on the opposite end of the cut vector. Upon ligation of these overhangs, not only will the second DNA sequence be inserted into the vector adjacent to the first DNA sequence in the desired orientation, but the restriction site at the second end of the second sequence will also be regenerated. Recreation of this restriction site will allow insertion of a further DNA sequence.

Any number of additional DNA sequences of interest may then be inserted into the vector sequentially from the second DNA sequence following the same protocol described for the second sequence.

In accordance with this discovery, it is an object of this invention to provide a method for directionally inserting multiple DNA sequences into a single DNA vector in a desired orientation.

It is also an object of this invention to provide a method for preparing expression vectors containing a plurality of genes in a desired orientation for insertion into host cells and expression of all of the gene products therefrom.

Another object of this invention is to provide a method for creating multi-gene cassettes which can be used as single intact units and transferred into other vectors or host cells.

Yet another object of this invention is to provide a method for transforming host cells with multiple genes using a single transformation.

Other objects and advantages of this invention will become readily apparent from the ensuing description.

BRIEF DESCRIPTION OF THE DRAWINGS

FIG. 2. Diagram of pFSPME, an intermediate vector utilized-in construction of chimeric crt genes. The Erwinia crt open reading frames (crtE, crtB, and crtI) were subcloned into -this vector (utilizing the PmeI and XhoI sites) in order to fuse the coding regions with Tri5 promoter and terminator elements. The chimeric genes could then be excised from the vector using Draone and Sfione primers. Details of vector construction are described in the Experimental Protocol.

FIG. 3. Gene cassette construction strategy. pCRTEX1 was created by cloning EcoRI digested insert#1 into EcoRI/SmaI digested BluescriptII KS$^-$. pCRTEX2 was created by directionally cloning DraIII/SfiI digested insert#2 into SfiI digested pCRTEX1; pCRTEX3 was subsequently created by cloning insert#3 into pCRTEX2. The gene cassette can be liberated from the vector sequences by NotI digestion, and cloned into alternate transformation vectors.

FIG. 4. Transformation plasmids for *Fusarium sporotrichioides*. pA1L-E (top) and p4AL-I (center) contain the *Aspergillus nidulans* amdS gene under the control of the native *A. nidulans* amdS promoter (pA1L-E), or under the control of the *Heterostrophus cochlibolus* Promoter 1 element (pA4L-I). pHL-J had the hygB genedriven by the Promoter 1 element. The direction of art gene transcription is denoted by the arrow direction.

DEFINITIONS

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage, cosmid, artificial chromosome (bacterial or yeast), or nucleic acid sequence which is able to replicate in a host cell, characterized by one or a small number of restriction endonuclease recognition sites at which the sequence may be cut in a predetermined fashion, and which may contain an optional marker suitable for use in the identification of transformed cells, e.g., tetracycline resistance or ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eukaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Cassette. A nucleic acid sequence within a vector which is to be transcribed, and a promoter to direct the transcription. The expression cassette may contain one or more unrelated DNA sequences encoding one or more peptides of interest.

Expression Vector. A replicon such as a plasmid, virus, retrovirus, bacteriophage, cosmid, artificial chromosome (bacterial or yeast), or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G. C, and uracil ("US").

Operably Encodes or associated. Operably encodes or operably associated each refer to the functional linkage between a promoter and nucleic acid sequence, wherein the promoter initiates transcription of RNA. corresponding to the DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Phage or Bacteriophage. Bacterial virus many of which include DNA sequences encapsidated in a protein envelope or coat ("capsid"). In a unicellular organism a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant."

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which: ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Replicon. Any genetic element (e.g., plasmid, chromosome, virus) that functions as an autonomous unit of DNA replication in vivo, i.e., capable of replication under its own control.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and yeast, for example, the exogenous DNA may be maintained on an episomal element such as a plasmid. With respect to eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

In the following description, the nomenclature used to define the proteins is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The invention can be used to insert any number or combination of native or foreign or heterologous DNA sequences into DNA vectors. These DNA sequences may be of any composition or function, they may encode proteins, polypeptides, regulatory elements, promoters, markers, and other non-protein producing DNA, or RNA of interest from eukaryotic or prokaryotic sources or from viruses. Moreover, DNA sequences or their encoded proteins, polypeptides, or RNA may have related functions, such as different enzymes involved in a common metabolic pathway, or they may be unrelated. Without being limited thereto, DNA sequences which may be incorporated into vectors for use herein may encode intracellular proteins, membrane proteins, and/or proteins secreted into the culture medium. The DNA sequences may encode proteins of interest corresponding to all or part of native proteins found in nature. The encoded proteins may also include chimeric proteins, for example, fused polypeptides or those from mutants displaying modified biological properties. Specific examples of proteins of interest which may be encoded by the DNA sequences herein include: pharmaceuticals or veterinary agents such as cytokines, hormones, or anticoagulants, enzymes, enzyme inhibitors, and antigens or vaccines. In the preferred embodiment, the DNA sequences which are used herein will encode a plurality of enzymes involved in a common metabolic or biosynthetic pathway for converting a precurser molecule into a product of interest. Examples include but are not limited to the enzymes of the carotenoid biosynthetic pathway as described in the Examples hereinbelow.

A plurality of any of these DNA sequences may be sequentially and directionally cloned or inserted in any desired orientation into a single vector. Furthermore, the sequences may be inserted in the same orientation (relative to their direction of transcription) in the vector, or in different orientations such as when a promoter is included with each inserted sequence. However, without being limited thereto, the DNA sequences are preferably inserted into the vector in the same orientation, with the direction of transcription (read from the 5' end to the 3' end of the coding strands) of each inserted sequence being the same.

In accordance with this invention, the orientation of insertion of multiple DNA sequences may be controlled by use of restriction sites which have a degenerate recognition sequence and which generate cohesive or overhanging ends upon cleavage by their corresponding restriction endonuclease. As used herein, it is understood that the term "restriction sites which have a degenerate recognition sequence" refers to restriction sites having specific user defined sequences, and which are cleaved by corresponding restriction endonucleases that recognize degenerate internal sequences therein. These restriction sites are added onto the ends of any two DNA sequences which are to be ligated, and the nucleotide sequences of the degenerate recognition sequences are chosen or tailored by the user such that the restriction sites will generate cohesive ends which are selectively complementary to each other. In the preferred embodiment, when using DNA sequences which encode proteins of interest, these complementary restriction sites will be added onto the adjacent upstream and downstream ends of the two sequences. However, as described above, it is also understood that the sequences may be inserted in the opposite orientation, with the downstream ends of each sequence being adjacent, or with their upstream ends adjacent. Unless otherwise specified, it is understood that in duplex DNA the terms "upstream" and "downstream" refer to the 5' and 3' directions from the coding strand, respectively.

In general, whenever it is desired to ligate any *second DNA sequence to a first DNA sequence, these restriction sites are selectively added onto the ends which are to be joined (preferably, but not limited to their upstream and downstream ends, respectively). By choosing the nucleotide sequences of the degenerate recognition sequences of these restriction sites such that the cohesive ends will be complementary only to each other, the directionality of the ligation of the DNA sequences to one another will be ensured. As described herein, it is understood that the description of cohesive ends as "complementary" refers to the ends as having overhangs of the same length and which are 100% complementary. Furthermore, as will be described in greater detail hereinbelow, by using the same restriction site on the ends of the sequences, the functional restriction site may be regenerated upon ligation into the vector, allowing its use for the insertion of additional restriction sites. Conversely, by using different restriction sites on the ends of the sequences, a functional restriction site is not regenerated.

A variety of restriction sites which contain degenerate recognition sequences and which generate cohesive ends upon cleavage as described above are known and are suitable for use herein. Without being limited thereto, preferred restriction sites include: DraIII, SfiI, PflMI, MwoI, BslI, BglI, and AlwNI. Each of these enzymes generate 3' cohesive ends with overhangs having a length of 3 nucleotides. Their recognition sequences and cleavage sites are as follows:

| Enzyme | Recognition Sequence | |
|---|---|---|
| DraIII | 5'... CACNNNGTG ... 3'<br>3'... GTGNNNCAC ... 5' | |
| SfiI | 5'... GGCCNNNNNGGCC ... 3'<br>3'... CCGGNNNNNCCGG ... 5' | (SEQ ID No. 17)<br>(SEQ ID No. 18) |
| PflMI | 5'... CCANNNNNTGG ... 3'<br>3'... GGTNNNNNACC ... 5' | (SEQ ID No. 19)<br>(SEQ ID No. 20) |
| MwoI | 5'... GCNNNNNNNGC ... 3'<br>3'... CGNNNNNNNCG ... 5' | (SEQ ID No. 21)<br>(SEQ ID No. 22) |
| BslI | 5'... CCNNNNNNNGG ... 3'<br>3'... GGNNNNNNNCC ... 5' | (SEQ ID No. 23)<br>(SEQ ID No. 24) |
| BglI | 5'... GCCNNNNNGGC ... 3'<br>3'... CGGNNNNNCCG ... 5' | (SEQ ID No. 25)<br>(SEQ ID No. 26) |
| AlwNI | 5'... CAGNNNCTG ... 3'<br>3'... GTCNNNGAC ... 5' | | where the cleavage sites are indicated by the arrows. It is understood that the restriction sites are not limited to these examples, and other restriction sites containing degenerate recognition sequences which generate cohesive ends of other lengths (such as overhangs of 4 nucleotides) may also be used. The degenerate region of the recognition sequence of any two of these sites (the same site or different sites) may be chosen such that they will generate selectively complementary cohesive ends upon cleavage. Corresponding restriction endonucleases are also commercially available from a variety of sources. These restriction enzymes typically cleave very infrequently in genomic DNA. However, the skilled practitioner will recognize that the specific restriction sites selected for use should not appear within the DNA sequences of interest.

The first DNA sequence to be inserted into the vector may be inserted using conventional techniques. Insertion of the first DNA sequence does not itself require the use of the above-mentioned restriction sites which contain a degenerate recognition sequence. The manner in which the first DNA sequence is inserted is not critical, and without being limited thereto, may include e ligation into vectors containing restriction sites generating blunt ends or cohesive ends upon cleavage, as described by Sambrook et al. (*Molecular Cloning: A laboratory Manual*, Cold Spring Harbor Laboratory Press, Plainview, N.Y., 1989), the contents of which are incorporated by reference herein. For example, in the preferred embodiment, the first DNA sequence of interest may be provided with a single restriction site generating a cohesive end at one end thereof, and the vector provided with any first restriction site generating a complementary cohesive end and a second restriction site generating a blunt end. The restriction site on the DNA sequence generating the cohesive end should of course be located at the appropriate end thereof to ensure insertion in the desired orientation. Alternatively, the first DNA sequence may be inserted into the vector by providing each of the vector and the ends of the DNA sequence with any restriction sites which generate complementary cohesive ends upon cleavage. When inserting the first DNA sequence in this manner, it is preferred that the restriction sites on the ends of the DNA sequence should be different. The DNA sequence may then be inserted into the vector in the desired orientation by cleaving these sites with their corresponding restriction enzymes, and ligating the resultant overhanging and/or blunt ends.

In accordance with this invention, to allow the insertion of any number of additional sequences adjacent to (upstream and/or downstream) the first DNA sequence, each in a desired orientation, one of the above-mentioned restriction sites which contain a degenerate recognition sequence and which generate cohesive ends upon cleavage is added adjacent to a selected end of the coding sequence of this first DNA sequence (i.e., at the end to which the additional sequences are to be added). This restriction site is distinct from and should be different from any restriction site(s) provided on the first DNA sequence to allow its insertion into the vector as described above. Moreover, it should be noted that if the first DNA sequence has any other restriction sites at the same end (such as sites used for inserting the sequence into the plasmid), the restriction site containing the degenerate recognition sequence must be positioned between those other sites and the DNA (coding) sequence.

To insert a second DNA sequence of interest adjacent to the first DNA sequence, the second DNA sequence, is also provided with a restriction site having a degenerate recognition sequence adjacent to a first end thereof (i.e., the end which is to be adjacent to the selected end of the first sequence described above) which, upon cleavage with its corresponding restriction enzyme, generates a cohesive end. The nucleotide sequences of the degenerate regions in each of these restriction sites on the selected end of the first DNA sequence and the first end of the second DNA sequence are selected such that the cohesive ends generated adjacent to the selected end of the first DNA sequence and the first end of the second DNA sequence upon cleavage, will be complementary and anneal to each other. However, it is also noted that while this restriction site on the first end of the second DNA sequence should also be selected from those restriction sites having an degenerate recognition sequence, it should not be the same as or identical to the downstream restriction site on the first DNA sequence (e.g., if one is SfiI, the other could be any of DraIII, PflMI, MwoI, BslI, BglI or AlwNI). By selecting different restriction sites that generate complementary cohesive ends, during ligation of the first and second DNA sequences the ends will anneal but a functional restriction site will not be regenerated. This will prevent inadvertent cleavage during the insertion of additional sequences.

If further DNA sequences are to be inserted adjacent to the second DNA sequence, the second DNA sequence should also include an additional restriction site adjacent to its opposite or second end, which is essentially the same as or identical to the above-mentioned restriction site on the selected end of the first DNA sequence. As defined herein, the restriction sites are "essentially the same" when they are the target sites for (cleaved by) the same restriction endonuclease, and the nucleotide sequences of the portions of the degenerate recognition sequences which form the cohesive ends upon cleavage are identical. It is envisioned that for those restriction sites having degenerate recognition sequences which extend upstream or downstream of the cleavage site (i.e., the degenerate recognition sequences are longer than the cohesive or overhanging ends) the degenerate nucleotides outside of the cleavage site may be different. Furthermore, the nucleotide sequences of the degenerate regions in these restriction sites are selected such that the cohesive end on the selected end of the first DNA sequence is not complementary to the cohesive end on the second end of the second DNA sequence.

Digestion of each of the restriction sites on the ends of second DNA sequence and the restriction site on the selected end of the first DNA sequence (now contained within the recombinant vector) with their corresponding restriction enzymes, and ligation of the resultant cohesive ends, will effectively insert the second DNA sequence into the vector adjacent to the first DNA sequence, oriented with the first end of the second sequence adjacent to the selected end of the first sequence. Because the restriction sites at the opposite ends of the second DNA sequence are different, when they are cleaved they will generate asymmetric cohesive ends, and each cohesive end will be complementary to only one of the ends on the digested vector. Directionality of the insertion in the desired orientation is therefore ensured.

Upon cleavage of the recombinant vector containing the first DNA sequence (at the restriction site at the selected end of the first sequence) to insert the second DNA sequence, cohesive ends will be created on both ends of the cut vector, one adjacent to the selected end of the first DNA sequence and the other at the opposite end of the vector. When the restriction sites on the second DNA sequence are cleaved, the restriction site adjacent to its first end will generate a cohesive end which is only complementary to the cohesive end adjacent to the first DNA sequence (at the selected end thereof), and the restriction site adjacent to its second end will generate a cohesive end which is only complementary to the cohesive end on the far end of the cut vector. When ligated, these cohesive ends will therefore not only anneal in the desired orientation, but the restriction site for the same restriction enzyme will also be regenerated at the second end of the second DNA sequence. Recreation of this restriction site will allow insertion of further DNA sequences adjacent to the second end of the second DNA sequence.

Any number of additional DNA sequences of interest may be added following the same protocol described for the second sequence. For instance, the third DNA sequence is also provided adjacent to a selected first end with a restriction site having a degenerate recognition sequence which generates a cohesive end upon cleavage with its corresponding restriction enzyme. Again, as with the second DNA sequence, the restriction sites on the second end of the second DNA sequence and the first end of the third DNA sequence should be different, but the nucleotide sequences of their degenerate regions within these restriction sites are selected such that the cohesive ends generated upon cleavage will be complementary and anneal to each other. As before, digestion of the third DNA sequence and the second DNA sequence (also now contained within the recombinant vector) with their corresponding restriction enzymes and annealing the resultant cohesive ends, inserts the third DNA sequence into the vector adjacent to the second end of the second DNA sequence, again in the desired orientation. Furthermore, as described for the second DNA sequence, if more DNA sequences are to be inserted, the third DNA sequence should also include a restriction site adjacent to its opposite or second end which is identical to the restriction site on the second end of the second DNA sequence. Still more DNA sequences may then be inserted in the same manner.

Alternatively, if no further DNA sequences are to be inserted, the addition of a downstream restriction site on the last inserted DNA sequence, although preferred, is not critical and may even be optional. If omitted, the manner of annealing the downstream end of the last DNA sequence to the far end of the cut vector may be performed using a variety of techniques. For instance, a restriction site generating a blunt end may be provided in the vector upstream or downstream from the from the point of insertion of the above-mentioned DNA sequences. Cleavage with its corresponding restriction enzyme will therefore remove the overhang previously generated on the far end of the cut vector, allowing the second or free end of the last DNA sequence and vector to anneal. Conversely, any restriction site may be added to the second end of the last DNA sequence which, upon cleavage with its corresponding restriction enzyme, generates a cohesive end which is complementary to and capable of annealing to the cohesive end on the far end of the cut vector. If no other DNA sequences are to be inserted, this restriction site need not be identical to the restriction site on the selected end of the first DNA sequence, but need only generate a complementary cohesive end.

In an alternative embodiment, it is also understood that addition of DNA sequences is not restricted to only one end of the first DNA sequence but that DNA sequences may be inserted adjacent to both ends of the first DNA sequence. Insertion of one or more further sequences at the other end of the first DNA sequence is conducted using the same process described above, with one of the above-mentioned restriction sites having a degenerate recognition sequence being provided on the second end of the first DNA sequence (opposite from the selected end). This restriction site should of course be different from the restriction site at the selected end. The further DNA sequence to be inserted is then provided with restriction sites in the same manner as the above-described second DNA sequence, except that the restriction sites at the ends of the further DNA sequence are selected relative to the restriction site at the second end of the first sequence.

The above-described restriction sites may be selectively added onto the upstream and/or downstream end of any DNA sequence of interest using Polymerase Chain Reaction (PCR) techniques or via incorporation using oligonucleotide linkers with the desired sites., PCR techniques are well known, and are described, for example, in Sambrook et al. (ibid), U.S. Pat. No. 4,683,195, and in *Current Protocols in Molecular Biology*, Ausubel et al. (eds.) Greene Publishing Assoc. And Wiley-Interscience, 1991, volume 2, chapter 15. In the preferred embodiment, the 5' and 3' PCR primers for the coding regions of the DNA sequences of interest are designed containing the selected restriction sites at their termini. Upon completion of amplification, the resultant DNA sequences will contain the selected restriction sites at their upstream and downstream ends. Details of this process are described in the Examples.

The vector selected should possess appropriate restriction sites for insertion of the DNA sequences of interest. A large number of vectors having polycloning sites are widely available and are suitable for use herein. Within each specific vector, various restriction sites may be generally selected for insertion of the isolated DNA sequences. Alternatively, specific restriction sites of interest may be inserted into a vector for subsequent cloning or expression of the DNA sequences of interest, using known techniques such as described by Kleid et al. (U.S. Pat. No. 5,888,808).

The particular site chosen for insertion of the selected DNA sequences into the vector to form a recombinant vector is determined by a variety of factors recognized by those of skill in the art. None of these factors alone absolutely controls the choice of insertion site for particular polypeptides. Rather, the site chosen reflects a balance of these factors, and not all sites may be equally effective for given proteins.

The DNA sequences of the invention may be inserted into the desired vector by known techniques. If the vector is to serve as an expression vector, it should have or be provided with a promoter, and the DNA sequences should be inserted in the vector downstream of the promoter and operably associated or linked therewith. The promoter should be operable in the host cell into which it is to be inserted (that is, the promoter should be recognized by the RNA polymerase of the host cell). While control sequences may be present with or ligated to the DNA coding sequence(s) prior to insertion into the vector, alternatively, a vector may be selected which already possesses an operable promoter. In addition, the vector may optionally have a region which codes for a ribosome binding site positioned between the promoter and the site at which the DNA sequence is inserted so as to be operably associated with the DNA sequence of the invention once inserted (in correct translational reading frame therewith). Moreover, the vector should preferably be selected to provide a region which codes for a ribosomal binding site recognized by the ribosomes of the host cell into which the vector is to be inserted. The vector may also optionally contain other regulatory sequences such as enhancer sequences, polyadenylation signals, transcription termination signals, or regulatory domains for effecting transcription and translation of the inserted coding sequences, or selectable markers as are known in the art, such as antibiotic resistance. The various DNA sequences of interest may be inserted with separate control elements, or under the control of a single promoter. The former is generally preferred when transforming eukaryotic host cells.

In the preferred embodiment, the DNA sequences of interest are inserted sequentially into the vector as described above and in the Examples. However, it is envisioned that the DNA sequences may be first ligated together in the desired order, and the resultant "cassette" inserted into the vector in a single step.

In an alternative embodiment, additional restriction sites may be provided in the vector, one on each side flanking the region in which the DNA sequences are inserted. Upon completion of insertion of the DNA sequences, cleavage of these sites enables the ligated sequences to be extracted as a single "cassette" for insertion into a different vector. These additional restriction sites may be present in the vector prior to insertion of the sequences, or they may be inserted with the first and last inserted DNA sequences (e.g., one present upstream from the first DNA sequence and the second present downstream from the last DNA sequence), or a combination thereof.

A variety of vector-host cell expression systems may be employed in practicing the present invention. Host cells may be either procaryotic or eukaryotic, and, when the host cells are bacterial cells, they may be either gram-negative or gram-positive bacteria. Strains of *Escherichia coli* are generally preferred for use in procaryotic systems. However, without being limited thereto, other useful hosts include species of Salmonella (including, for example, *S. typhimurium*, *S. enteriditis*, and *S. dublin*) species of Mycobacterium (such as *M. smegmatis* and *M. bovis*, species of Pseudomonas (including, for example, *P. aeruginosa* and *P. putida*), *Bacillus subtilis*, yeasts and other fungi (for example, *Saccharomyces cerevisiae*), plant cells such as plant cells in culture (including, for example, both angiosperms and gymnosperms) and animal cells such as animal cells in culture.

Vectors used in practicing the present invention are selected to be operable as cloning vectors or expression vectors in the selected host cell. While plasmid vectors are preferred, the vector may, for example, be a virus, retrovirus, bacteriophage, cosmid, artificial chromosome (bacterial or yeast), or any nucleic acid sequence which is able to replicate in a host cell. Numerous vectors, including plasmids, are known to practitioners skilled in the art, and selection of an appropriate vector and host cell is a matter of choice. A number of procaryotic plasmid expression vectors are described in U.S. Pat. Nos. 4,652,525, 4,440,859, 4,436,815, and 4,342,832, and a number of eukaryotic plasmid expression vectors have also been described in U.S. Pat. Nos. 4,546,082, 4,510,245, 4,446,235, and 4,443,540. Further, the vectors may be non-fusion vectors (i.e., those producing polypeptides of the invention not fused to any heterologous polypeptide), or alternatively, fusion vectors (i.e., those producing the polypeptide fused to a vector encoded polypeptide). The fusion proteins would of course vary with the particular vector chosen. Suitable non-fusion plasmid vectors for use with *E. coli* include but are not limited to pTrc99, for use with, *E. coli* JM 105, or pANK-12, pANH-1 or pPL2 for use with *E. coli* MZ 1. Conversely, suitable fusion plasmid vectors include pGEX and pMC1871 for use with *E. coli* JM 105, pMAL with *E. coli* PR 722, pVB2 with *E. coli* LA5709, pTrcHis with *E. coli* INV F', pCO5 with *E. coli* N6405, and pRIT2T or pEZZ 18 with *E. coli* N4830-1. Other, non-*E. coli* expression systems which may also be employed include pAc360 or pBluescript for use with SP2 or High 5 insect cells, pYesHis with the yeast *S. cerevisiae* INVSc1 or INVSc2, pLS405 with *Salmonella dublin* SL598, and pYUB12 with *Mycobacterium smegmatis* or *M. bovis*. Still other suitable plasmid vector-host combinations that may be used in practicing the instant invention are described, for example, in U.S. Pat. Nos. 5,122,471 and 5,670,339 the contents of each of which are incorporated by reference herein.

The proteins and polypeptides encoded by the inserted DNA sequences in this are expressed by growing host cells transformed by the expression vectors described above under conditions whereby the proteins or polypeptides are expressed. They may then be isolated from the host cells if desired. Depending on the host cell used, transformation is done using standard techniques. For example, the calcium treatment employing calcium chloride, described by Cohen (1972, Proc Natl Acad Sci USA, 69:2110), or the RbCl method, described in Sambrook et al. (ibid) may be used for prokaryotes or other cells which contain substantial cell wall barriers. Infection with *Agrobacterium tumefaciens* such as described by Shaw (1983, Gene, 23:315) may be used for certain plant cells. For mammalian cells without such cell walls, the calcium phosphate precipitation method of Graham and Van der Eb (1978, Virology, 52:546), or electroporation described in Sambrook et al. (ibid), may be used. Transformations into yeast may be conducted, for example, according to the method of Van Solingen, et al., (1977, J. Bacter., 130:946), and Hsiao et al. (1979, Proc Natl Acad Sci USA, 76:3829).

In general, after construction of a suitable expression vector, the vector is transformed into the appropriate host and successful transformants may be selected by markers contained on the expression vectors. Successfully transformed colonies are then cultured in if order to produce the proteins or polypeptides, or to produce cells having a well-defined number of copies of DNA elements of interest.

The following examples are intended only to further illustrate the invention and are not intended to limit the scope of the invention which is defined by the claims.

EXAMPLE 1

To determine the utility of Tri5⁻ as a host strain for foreign isoprenoid production, we introduced three genes from the *Erwinia uredovora* carotenoid biosynthetic pathway into a strain of *Fusarium sporotrichoides* (NRRL 3299). In this strain the production of trichothecenes, a family of toxic sesquiterpenoid epoxides, represents a significant amount of total isoprenoid pathway carbon flow. Trichothecene production in *F. sporotrichioides* (NRRL 3299), under specific growing conditions, can constitute as much as 10 to 20% of culture fresh weight. This high level of isoprenoid pathway biosynthetic capacity, if diverted from trichothecene production, could potentially be utilized in the production of commercially valuable isoprenoid compounds.

The first committed step of trichothecene production, the cyclization of farnesyl diphosphate to form trichodiene, is catalyzed by the sesquiterpene synthase trichodiene synthase (Tri5). The gene (and flanking sequences) coding for trichodiene synthase in *F. sporotrichioides* has been cloned and characterized (Hohn and Beremand, 1989, Gene, 79:131–138). Using gene disruption of Tri5, a trichothecene deficient mutant of NRRL 3299 has been generated (designated as $Tri5^-$). This mutant strain of *F. sporotrichioides* afforded us with the opportunity to examine the feasibility of channeling isoprenoid precursors formerly used for trichothecene biosynthesis into the production of heterologous isoprenoids.

Although trichothecene and carotenoid biosynthesis share the common precursor farnesyl diphosphate, the production of carotenoids requires the catalytic activity of enzymes not normally present in *F. sporotrichioides*, or which are expressed at very low levels. To introduce these genes via individual transformations would have been technically tedious, and the number of transformations limited by the small number of selectable markers available for use in this species. In earlier work (Jones et al., 1996, "Metabolic engineering of trichothecne-producing Fusarium", Society for Industrial Microbiology Annual Meeting Abstracts, 1996, P15), we discovered that NRRL 329.9 (and $Tri5^-$) were resistant to the commonly used selective agents bialaphos and phleomycin, but were unable to grow on the alternate nitrogen source acetamide. This permitted us to utilize transformation methods using the *Aspergillus nidulans* amdS gene as a selectable marker.

The process of this invention for the directional cloning of multiple genes was used to simultaneously introduce three genes required for the synthesis of the carotenoid lycopene from farnesyl diphosphate. These genes, under the control of Tri5 promoter and terminator elements, produced functional enzymes when expressed in *E. coli*, and were expressed at high levels in certain Fusarium transformants.

Experimental Protocol

Cloning of Erwinia crt coding regions

The following PCR primers were used to clone the crt genes from Erwinia genomic DNA: 5'TCCCCCGGGCAATATGACGGTCTGCG-CAAAAAAACACG3' (crtE sense), 5'CCGCTCGAG-CATCCTTAACTGACGGCAGCG3' (crtE antisense), 5'TCCCCCGGGCAATATGGCAGTTGGCTC-GAAAAGTT3' (crtB sense), 5'CCGCTCGAGGTTG-TATATGGCGCACCGTATGC3' (crtB antisense), 5'TCCCCCGGGCAATATGAAACCAACTACG-GTAATTGG3' (crtI sense), and 5'CCGCTCGAGACGGAT-TATTCAAATCAGATCCTCC3' (crtI antisense) (SEQ ID Nos. 1–6, respectively). The sense primers contained SmaI recognition sites, while the antisense primers contained XhoI recognition sites. PCR reactions were done according to manufacturer's protocol (Pfu polymerase, Stratagene, La Jolla, Calif.). Purification of PCR products was done using Qiaquick spin columns (Qiagen, Santa Clarita, Calif.); following purification, DNA was digested with SmaI and XhoI (all restriction enzymes obtained from New England Biolabs, Beverly, Mass.), and ligated into PmeI/XhoI digested pFSPME1. pFSPME1 was derived from pFS22-1 (Hohn and Beremand, ibid) by deletion of the Tri5 coding region and introduction of PmeI and XhoI sites at the promoter and terminator termini, respectively.

Assembly of art cassette

Chimeric Tri5crtE was excised from pFSPME1 using the following PCR primers: 5'GGAATTCGCGGCCGCTACA-GATTCCCGCACAAAGGAA3' (CrtE5) and 5'GGC-CGAAAGGGCCAAACTCGGTGTAAAA-CAAGTTCCC3' (Sfione) (SEQ ID Nos. 7 and 8, respectively). Following purification of the PCR product, DNA was digested with EcoRI and ligated into EcoRI/SmaI digested BluescriptII KS (Stratagene, La Jolla, Calif.), producing pCRTEX1. Tri5crtB and Tri5crtI were excised from pFSPME1 using the primers: 5'GCACTTTGTGAGTACAGATTCCCGCACAAAG3' (Draone) (SEQ ID No. 9) and Sfione. After digestion with DraIII and SfiI, the two genes were sequentially ligated into SfiI digested pCRTEX1, producing the plasmids pCRTEX2 and pCRTEX3. The crt cassette was excised from pCRTEX3 by NotI digestion, and ligated into transformation vectors containing amdS (pA1L-E and pA4L-I) or hygB (pHL-J) selectable markers.

ProtoPlast Isolation and Transformation Protocols

Protoplast isolation and transformation of NRRL 3299 with the transformation vector pHL-J followed the protocols described by Hohn, et al. (1993, Curr. Genet. 24:291–295). Protoplast isolation and transformation of Tri5⁻ with the transformation vectors pA1L-E and pA4L-I followed the protocols described Royer et al. (1995, Bio/technology, 13:1479–1483) with the following modifications. Germinated spores were digested with a mixture of Novozyme 234 (5 mg/mL), Driselase (25 mg/mL), and chitinase (0.05 mg/mL) in 0.7 m NaCl. Protoplasts were collected by centrifugation, washed twice with STC (1.4M sorbitol, 10 mM Tris-HCl pH 7.5, 50 mM $CaCl_2$), and diluted to a concentration of $1\times10^8$ protoplasts/mL in RSTC-:SPTC:DMSO [8.0:2.0:0.1] (RPTC =0.8M sorbitol, 50 mM Tris-HCl pH8, 50 mM $CaCl_2$; SPTC=40% PEG 4000, 0.8M sorbitol, 50 mM Tris-HCl pH8, 50 mM $CaCl_2$).

PCR analysis of transformants

PCR reactions were performed as per manufacturer's recommendations (Taq polymerase, Promega, Madison, Wis.). To ascertain the presence of the amdS selectable marker in E and I transformants, the following primers were used:
5'GGGACTCGGTTCTGACAACC3' (sense) and 5'CCGAAATCGTGCTTGTATGG3' (antisense)(SEQ ID Nos. 10 and 11, respectively). The anticipated product size with these primers was approximately 700 bp. To determine the integrity of the introduced crt gene cassette, the crtE sense and crtI antisense primers were utilized (product size 5.6 Kb). To determine the presence of the individual Tri5crt genes in the transformants, Draone and the respective crt antisense primer were used in the PCR reaction.

DNA and RNA analysis

DNA was isolated from cultures grown in YPG medium (0.3% yeast extract, 1% peptone, 2% glucose), following manufacturers protocols (Genomic Tip-100, Qiagen, Santa Clarita, Calif.). RNA was isolated from cultures grown in GYEP medium (5% glucose, 0.1%. yeast extract, 0.1% peptone), following manufacturer's protocol (TRIZOL Reagent, GibcoBRL Life Technologies). Southern blotting was performed according to the protocol of Hohn and Desjardins (Hohn and Desjardins, 1992, Mol. Plant-Microbe Interact., 5:249–256). RNA blotting was performed as described by Proctor and Hohn (1993, J. Biol. Chem., 268:4543–4548).

Analysis of lycopene content

Liquid cultures were analyzed for lycopene by high-performance liquid chromatography (HPLC). Mycelia filtered from 25-ml liquid shake cultures in GYEP medium were ground in liquid nitrogen in a mortar and pestle, and added to 50 ml Oakridge tubes containing 20 ml of hexane:EtOH (2:1). Samples were incubated 30 minutes @ 37° C., and layers separated by centrifugation. The organic phase was removed, dried under nitrogen gas stream, and reconstituted in 500 $\mu L$ methyl tert-butyl ether (MTBE). Lycopene was detected by HPLC using a YMC Carotenoid C30 reverse-phase column. Lycopene was eluted using a mobile phase of methanol/MTBE, with a gradient of 30–75% MTBE in 40 minutes. Flow rate was 1.0 ml/minute. Detection of lycopene was done at 470 nm using a Spectraflow 783 Programmable Absorbance Detector (Kratos Division, ABI Analytical, Ramsey, N.J.).

Results and Discussion

Construction of chimeric carotenoid biosynthetic genes

The carotenoid biosynthetic genes introduced into *F. sporotrichioides* were crtE (geranylgeranyl pyrophosphate synthase), crtB (phytoene synthase), and crtI (phytoene desaturase). The enzymes encoded by these genes catalyze the conversion of two molecules of farnesyl diphosphate into a molecule of the carotenoid lycopene. The coding regions for these enzymes were isolated from the *Erwinia uredovora* crt cluster (Misawa et al., J. of Bact., 172:6704–6712), utilizing the polymerase chain reaction or PCR (primers and PCR conditions detailed in the Experimental Protocol). The PCR primers used included the recognition sites for the restriction enzymes SmaI (on the sense primers) and XhoI (on the antisense primers); following purification, the PCR products were digested with SmaI and XhoI and directionally cloned into PmeI/XhoI digested pFSPME1. (FIG. 2). This plasmid contains both the 5' and 3' flanking regions of Tri5 from *F. sporotrichioides*. This procedure was done for all three Erwinia crt coding regions, producing chimeric versions of crtE, crtB, and crtI (Tri5crtE, Tri5crtB, and Tri5crtI). Each chimeric gene possessed approximately 730 bp of the Tri5 promoter, and 360 bp of 3' sequence (including the transcription stop signal).

Design of Compatible DraIII/SfiI Overhangs

Figure 1:
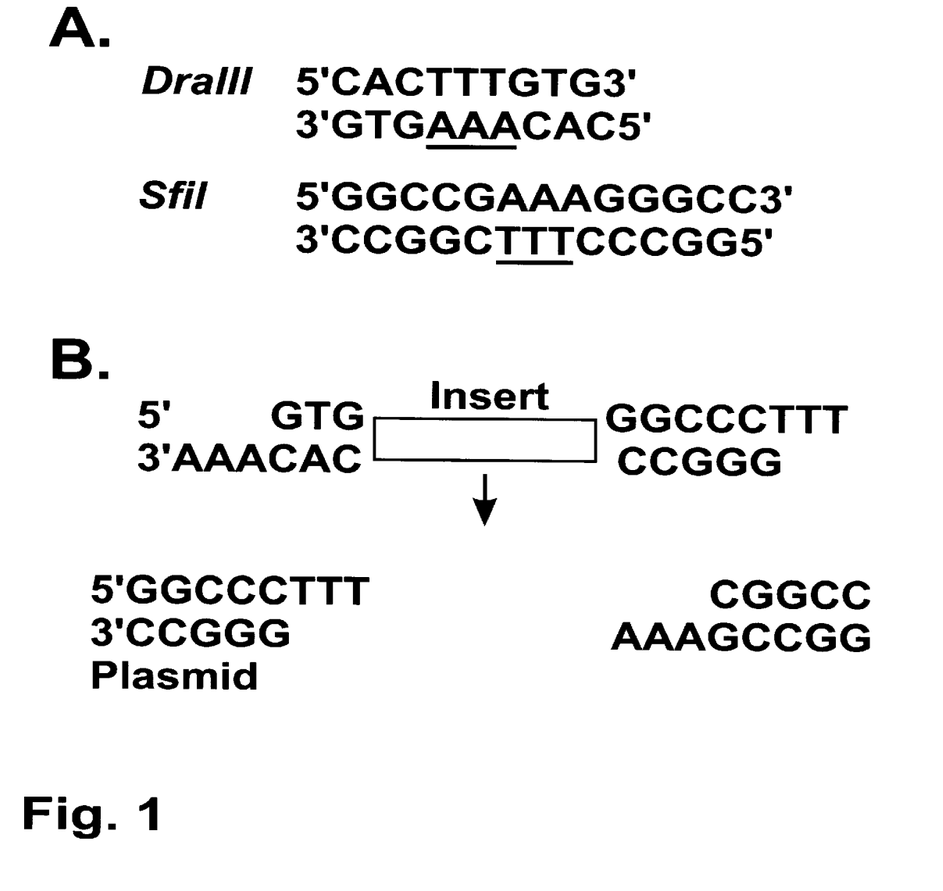
FIG. 1 (Panels A–B). Description of DraIII and SfiI linkers used to directionally clone PCR products. Panel A depicts the sequence of the DraIII and SfiI linkers added to the termini of PCR primers. Panel B shows the ligation of a DraIII/SfiI digested insert into a SfiI digested vector. The uppermost SfiI linker corresponds to nucleotides 1–13 of SEQ ID No. 8, while the lowermost SfiI linker corresponds to Seq ID No. 16.
Figure 2:
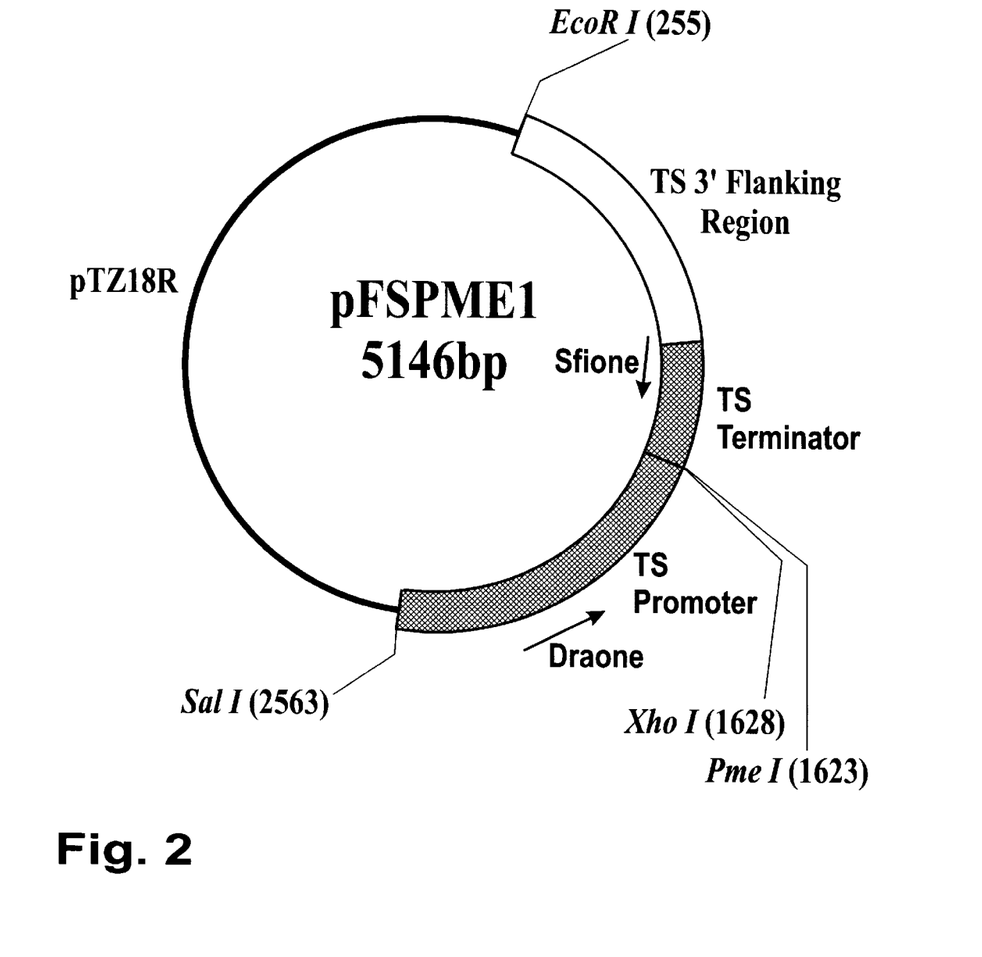

FIG. 1 illustrates the DraIII and SfiI sites that were designed for the primers used in our cloning strategy. PCR primers containing sequences complementary to the desired target are designed containing DraIII and SfiI sites at the 5' and 3' ends, respectively (shown in Table 1). The 3' AAA extension generated by DraIII extension can only be ligated to the 3' (TTT) extension of a digested SfiI site on the plasmid, thus ensuring the directionality of the insertion events. Other extensions could also be designed to give the desired. result (i.e., CAC, TCT, CAT), but this was the nucleotide sequence used in our studies. The ligation of the DraIII cohesive end with a SfiI cohesive end produces a sequence uncleavable by either enzyme; however, the ligation of the two SfiI cohesive ends regenerates a sequence recognizable by SfiI.

Creation of the Gene Cassette

There are two options as to how the gene cassette is initiated. One method would be to simply introduce the first insert (with DraIII and SfiI sites at the 5' and 3'termini, respectively) into a vector digested with a restriction enzyme that produces blunt ends (e.g., EcoRV). Further inserts could then be added by digesting the inserts with DraIII and SfiI, followed by ligation into SfiI-digested vector. Depending on the availability of restriction sites flanking the growing cassette, it may be problematic when attempting to move the cassette from one vector to another. To avoid this problem, we utilized the strategy outlined in FIG. 3. The first insert was amplified using primers which contained EcoRI and NotI sites on the primer for the 5' end of the insert (Eco/Not), while a SfiI site was present on the primer for the 3' end of the insert (Sfione). This PCR product was digested with EcoRI, and cloned into EcoRI/SmaI digested BluescriptII KS−. This allowed us to take advantage of the NotI site present in the MCS of the plasmid; by adding an additional NotI site via PCR, we were able to flank the cassette with NotI sites, which could be utilized to excise the cassette and move it into alternate vectors (NotI is not present in any of our insert sequences).

Figure 3:
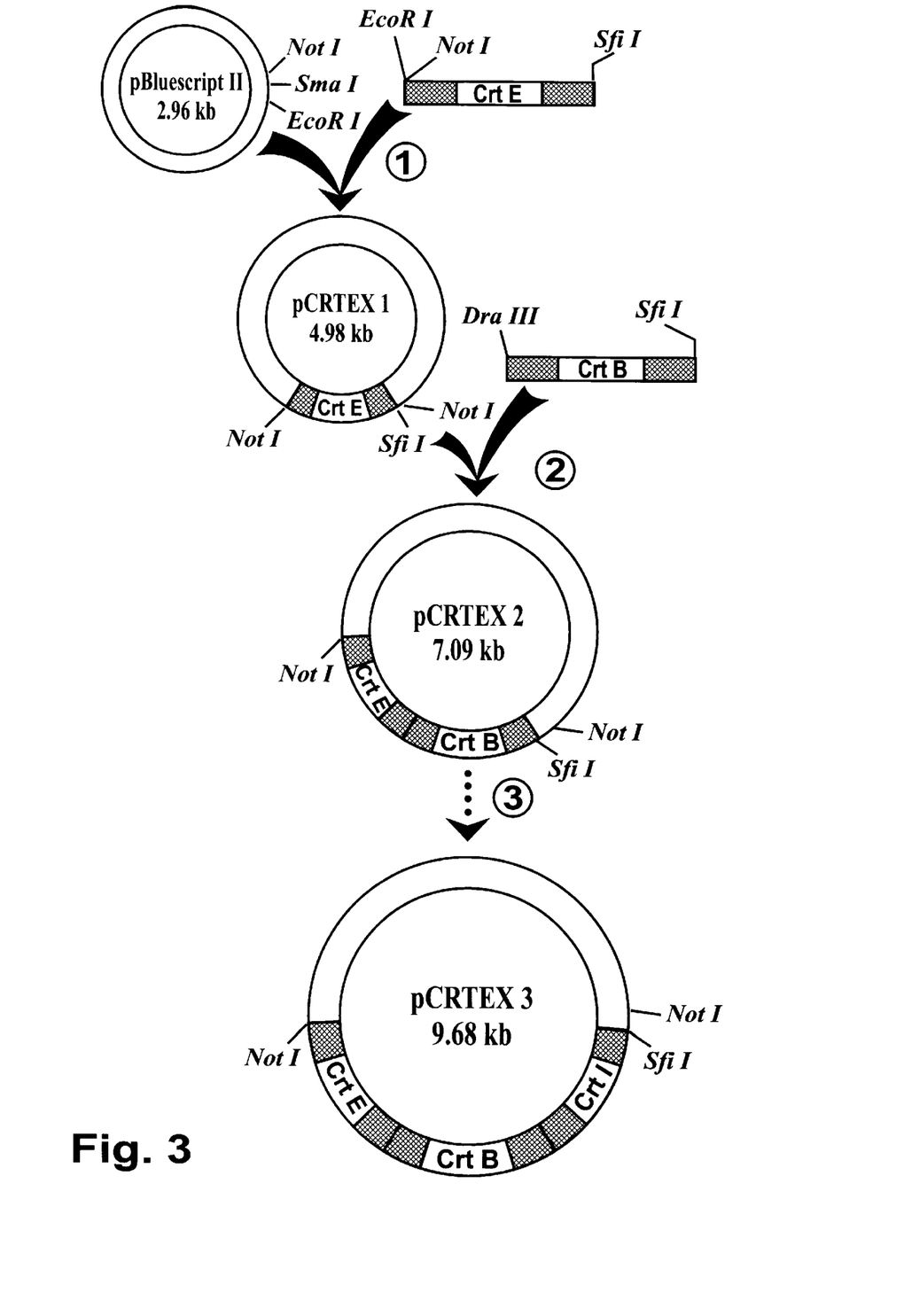

Once the first insert is in place in the vector, additional inserts can be added by digesting the inserts with DraIII and SfiI, and cloning the fragments into the SfiI-digested vector. Upon ligation of insert and vector, a SfiI site is preserved at the 3' end of the cassette, and additional inserts can be added as shown. To date, we have successfully cloned 4 genes (comprising approximately 9 Kb) in tandem in a single vector. Although our inserts share a great deal of repeated sequence (due to possessing the same promoter and terminator sequences), we have not observed any problems with recombination within similar sequences while the plasmids are being maintained in E. coli. Furthermore, we have excised the gene cassette (using NotI) and introduced it into a number of transformation vectors used in our laboratory; this is a tremendous improvement over having to clone the sequences into each vector independently. Using this cloning strategy also reduces the number of transformations necessary to introduce the desired genes into a target organism (Fusarium sporotrichioides in our case); this is especially important when only a limited number of selectable markers are available for transformations.

Figure 4:
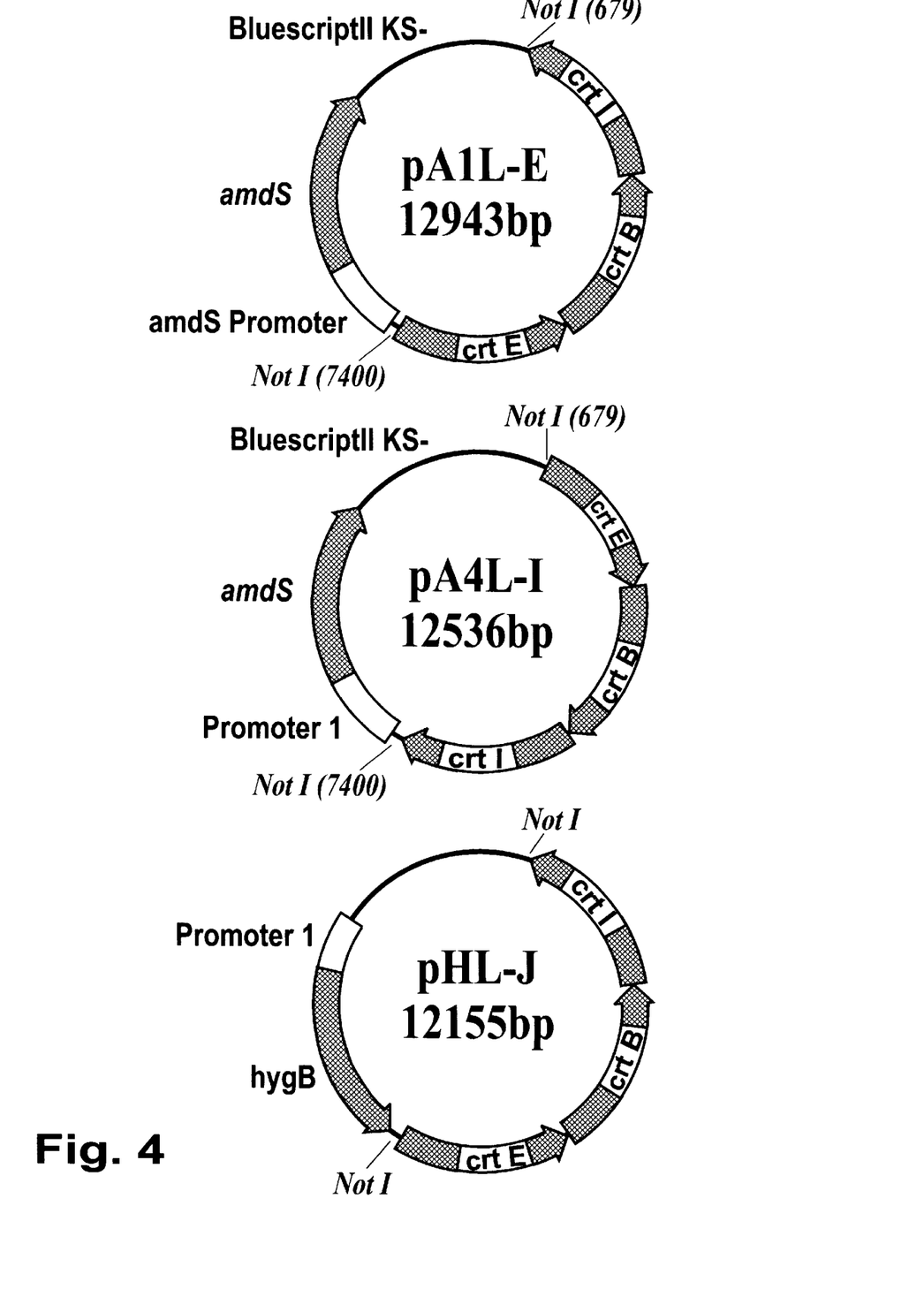

After the insertion of Tri5crtE, Tri5crtB, and Tri5crtI, the crt gene cassette was excised by NotI digestion, and cloned into transformation vectors containing either amdS (for Tri5−) or hygB (for NRRL 3299) selectable markers. The resultant plasmids, designated pA1L-E, pA4L-I, and pHL-J, are depicted in FIG. 4.

Analysis of Fusarium transformants

Using transformation protocols detailed in the Experimental Protocol, the transformation vectors carrying the crt cassette were introduced into competent F. sporotrichioides protoplasts, resulting in 6 transformants from NRRL 3299 protoplasts (J transformants), and 11 transformants from Tri5− protoplasts (E and I transformants). Preliminary analysis of the primary transformants indicated a high level of untransformed nuclei were present in the amdS transformants (E and I). Single spore purification of the primary transformants was necessary to examine whether the introduced genes were being properly expressed. This purification was accomplished for all but two of the E transformant lines. PCR analysis demonstrated that the crt gene cassette was integrated as an intact unit in 6 of the transformants, with the remaining transformants (with the exception of J6) missing either one or two of the introduced genes, presumably due to various recombination events which occurred between the trichodiene synthase elements of the chimeric genes and the endogenous trichodiene synthase sequences in Fusarium. Interestingly, transformant J6 contained,all three introduced genes, but not as an intact unit. Southern analysis confirmed the results of the PCR analysis.

RNA analysis of single spore purified transformants demonstrated the presence of Tri5crtE, Tri5crtB, and Tri5crtI transcripts (corresponding to geranylgeranyl-pyrophosphate synthase, phytoene synthase, and phytoene desaturase, respectively). Expression of transgenes was similar to that of Tri4 expression. Tri4, a cytochrome P450 monooxygenase involved in trichothecene biosynthesis (Hohn et al., 1995, Mol. Gen. Genet., 248:95–102), is expressed at levels similar to Tri5 under the culture conditions used. This result demonstrated that the Tri5 promoter used in creating Tri5crtE, Tri5crtB, and Tri5crtI was of sufficient size to obtain optimal transgene expression. Previously studies have demonstrated that Tri5 (and Tri4) RNA levels are induced over 50-fold after 24 h of culture of NRRL 3299 in GYEP H medium. The pattern of transgene expression correlated with earlier PCR data (Jones et al., 1996, Metabolic Engineering of Trichothecene-producing Fusarium, Society for Industrial Microbiology Annual Meeting Abstracts, P15); the number of transgene transcripts equaled the number of carotenoid biosynthetic genes that were detected within each individual transformant.

Analysis of carotenoid expression in E. coli and Fusarium transformants

Lycopene production was observed in crt gene cassette-carrying E. coli, and in Fusarium transformants. Lycopene production was first observed after 3 days of culture, with maximum production observed in 5 to 6 day old cultures (~0.5 mg/g culture dry weight).

Four of the preferred lycopene producing strains of transformed Fusarium sporotrichioides, designated E22e, I8d, I91a, and J62, were retained. All four strains have been deposited under the Budapest Treaty in the United States Department of Agriculture Agricultural Research Service culture collection in Peoria, Ill., on Jul. 1, 1999, and have been assigned deposit accession numbers NRRL 30156, NRRL 30155, NRRL 30154, and NRRL 30153, respectively.

In summary, we have developed a strategy using complementary DraIII/SfiI restriction sites to directionally clone multiple genes into Fusarium sporotrichioides, with each gene under the control of an active (Tri5) Fusarium-specific promoter. We are currently expanding the size of our cassette, thereby increasing the number of carotenoid products which can be produced. In our current study, approximately 40% (6/17) transformants contained an intact crt gene cassette. It is reasonable to assume that as the number of genes in the cassette increases, the likelihood of trichodiene synthase elements recombination with endogenous sequences also increases, leading to loss of one or more of the introduced genes. We have been able to demonstrate that the chimeric genes are capable of producing functional enzymes, and high levels of chimeric gene expression were observed in some of the transformants. The results of this study demonstrate the feasibility of genetically engineering *Fusarium sporotrichioides* in order to utilize the species as a host for high level synthesis of commercially valuable isoprenoid products.

EXAMPLE 2

To increase the biosynthetic capabilities of Tri5-beyond lycopene production, a new cassette was constructed by the addition of crtY (downstream of the crtI gene in the cassette of Example 1), an *Erwinia uredovora* gene encoding for lycopene cyclase. This new, four gene cassette should permit the production of β-carotene in transformed Fusarium. CrtY was modified and inserted into the cassette as follows; the gene coding sequence was amplified from *E. uredovora* genomic DNA using Pfu polymerase and the following primers: CrtY5 (5' CCCGGGCAATATGCAACCGCAT-TATGATCTGATTC 3') and YREV6 (5' CGCTCGAGCCG-TAGTTGGTTTCATGTAGTCGC 3')(SEQ ID Nos. 12 and 13, respectively). After digestion with SmaI and XhoI, the fragment was ligated into pFSPME1. The chimeric crtY gene was then amplified using Pfu polymerase and Draone and Sfione primers, and after DraIII/SfiI digestion, the crtY gene was ligated into the existing three gene cassette.

The new four gene cassette was liberated from Bluescript using NotI digestion, and the cassette was ligated into a second plasmid, pAMDS4, to form pBCX-14. The cassette was also ligated into a new expression vector. This new vector, constructed from pAMDS4, contains Tri10 (upstream of the β-carotene cassette), a gene present in the Fusarium trichothecene gene cluster, which appears to have a role in regulating and enhancing expression of other Tri genes. Using PCR primers (#247: 5'GGTCAACATGATGT-CAGG 3'; #620: 5'CGCCAAGTACGTGGACCGGCTG-CACATGTCAAGG 3') (SEQ ID Nos. 14 and 15, respectively), the Tri10 gene was amplified from pTRI9D4-7 and inserted into pAMDS4. Upon addition of the four gene cassette, the resultant plasmid was named pTRIBCX-44.

pBCX-14 and pTRIBCX-44 were transformed into *Fusarium sporotrichioides* (Tri5−) protoplasts as previously described. Four independent transformants containing pBCX-14 (FS1-4) and 3 independent transformants containing pTRIBCX-44 (ST1-3) were single spore purified and analyzed further. The four gene cassette was found to be integrated as an intact unit in all seven transformants. β-carotene production was observed in FS and ST transformant strains. The greatest carotenoid production was observed in ST transformants, with yields reaching 3 to 4 mg β-carotene per gram of fungus (dry weight).

Three of the preferred β-carotene producing strains of transformed *Fusarium sporotrichioides*, designated ST1, ST2, and ST3, were retained. All three strains have been deposited under the Budapest Treaty in the United States Department of Agriculture Agricultural Research Service culture collection in Peoria, Illinois, on Jul. 15, 1999, and have been assigned deposit accession numbers NRRL 30157, NRRL 30158, and NRRL 30159, respectively.

It is understood that the foregoing detailed description is given merely by way of illustration and that modifications and deviations may be made therein without departing from the spirit and scope of the invention.

TABLE 1

Oligonucleotides added to insert sequence specific PCR primers for the purpose of introducing restriction endonuclease sites

| Primer Name | Added Sequence | Notes | Sequence Listing |
| --- | --- | --- | --- |
| Eco/Not | 5'GGAATTCGCGGCCGC3' | Primer for 5' end of first insert | Nuc. 1–15 of SEQ ID NO: 7 |
| Draone | 5'GCACTTTGTGAG3' | Primer for 5' end of remaining inserts | Nuc. 1–12 of SEQ ID NO: 9 |
| Sfione | 5'GGCCGAAAGGGCC3' | Primer for 3' ends of inserts | Nuc. 1–13 of SEQ ID NO: 8 |

We claim:

1. A transformed strain of *Fusarium sporotrichioides* effective for production of β-carotene selected from the group consisting of NRRL 30157, NRRL 30158, and NRRL 30159.

* * * * *

SEQUENCE LISTING

<160> NUMBER OF SEQ ID NOS: 26

<210> SEQ ID NO 1
<211> LENGTH: 38
<212> TYPE: DNA
<213> ORGANISM: Erwinia uredovora

<400> SEQUENCE: 1
tcccccgggc aatatgacgg tctgcgcaaa aaaacacg                38

<210> SEQ ID NO 2
<211> LENGTH: 30
<212> TYPE: DNA
<213> ORGANISM: Erwinia uredovora -continued
<210> SEQ ID NO 2
<211> LENGTH: 35
<212> TYPE: DNA
<213> ORGANISM: Erwinia uredovora

<400> SEQUENCE: 2
ccgctcgagc atccttaact gacggcagcg                                    30

<210> SEQ ID NO 3
<211> LENGTH: 35
<212> TYPE: DNA
<213> ORGANISM: Erwinia uredovora

<400> SEQUENCE: 3
tcccccgggc aatatggcag ttggctcgaa aagtt                              35

<210> SEQ ID NO 4
<211> LENGTH: 32
<212> TYPE: DNA
<213> ORGANISM: Erwinia uredovora

<400> SEQUENCE: 4
ccgctcgagg ttgtatatgg cgcaccgtat gc                                 32

<210> SEQ ID NO 5
<211> LENGTH: 36
<212> TYPE: DNA
<213> ORGANISM: Erwinia uredovora

<400> SEQUENCE: 5
tcccccgggc aatatgaaac caactacggt aattgg                             36

<210> SEQ ID NO 6
<211> LENGTH: 34
<212> TYPE: DNA
<213> ORGANISM: Erwinia uredovora

<400> SEQUENCE: 6
ccgctcgaga cggattattc aaatcagatc ctcc                               34

<210> SEQ ID NO 7
<211> LENGTH: 37
<212> TYPE: DNA
<213> ORGANISM: Fusarium sporotrichioides

<400> SEQUENCE: 7
ggaattcgcg gccgctacag attcccgcac aaaggaa                            37

<210> SEQ ID NO 8
<211> LENGTH: 37
<212> TYPE: DNA
<213> ORGANISM: Fusarium sporotrichioides

<400> SEQUENCE: 8
ggccgaaagg gccaaactcg gtgtaaaaca agttccc                            37

<210> SEQ ID NO 9
<211> LENGTH: 31
<212> TYPE: DNA
<213> ORGANISM: Fusarium sporotrichioides

<400> SEQUENCE: 9
gcactttgtg agtacagatt cccgcacaaa g                                  31

<210> SEQ ID NO 10
<211> LENGTH: 20
<212> TYPE: DNA
<213> ORGANISM: Aspergillus sp.

<400> SEQUENCE: 10
gggactcggt tctgacaacc                                           20

<210> SEQ ID NO 11
<211> LENGTH: 20
<212> TYPE: DNA
<213> ORGANISM: Aspergillus sp.

<400> SEQUENCE: 11
ccgaaatcgt gcttgtatgg                                           20

<210> SEQ ID NO 12
<211> LENGTH: 35
<212> TYPE: DNA
<213> ORGANISM: Erwinia uredovora

<400> SEQUENCE: 12
cccgggcaat atgcaaccgc attatgatct gattc                          35

<210> SEQ ID NO 13
<211> LENGTH: 32
<212> TYPE: DNA
<213> ORGANISM: Erwinia uredovora

<400> SEQUENCE: 13
cgctcgagcc gtagttggtt tcatgtagtc gc                             32

<210> SEQ ID NO 14
<211> LENGTH: 18
<212> TYPE: DNA
<213> ORGANISM: Fusarium sporotrichioides

<400> SEQUENCE: 14
ggtcaacatg atgtcagg                                             18

<210> SEQ ID NO 15
<211> LENGTH: 34
<212> TYPE: DNA
<213> ORGANISM: Fusarium sporotrichioides

<400> SEQUENCE: 15
cgccaagtac gtggaccggc tgcacatgtc aagg                           34

<210> SEQ ID NO 16
<211> LENGTH: 13
<212> TYPE: DNA
<213> ORGANISM: Fusarium sporotrichioides

<400> SEQUENCE: 16 ggcctttcg gcc                                                   13

<210> SEQ ID NO 17
<211> LENGTH: 13
<212> TYPE: DNA
<213> ORGANISM: Streptomyces fimbriatus
<220> FEATURE:
<221> NAME/KEY: variation
<222> LOCATION: (5)..(9)
<223> OTHER INFORMATION: n may be A, T, G, or C

<400> SEQUENCE: 17
ggccnnnnng gcc 13

```
<210> SEQ ID NO 18
<211> LENGTH: 13
<212> TYPE: DNA
<213> ORGANISM: Streptomyces fimbriatus
<220> FEATURE:
<221> NAME/KEY: variation
<222> LOCATION: (5)..(9)
<223> OTHER INFORMATION: n may be A, T, G, or C

<400> SEQUENCE: 18
ggccnnnnng gcc                                                          13

<210> SEQ ID NO 19
<211> LENGTH: 11
<212> TYPE: DNA
<213> ORGANISM: Pseudomonas fluorescens
<220> FEATURE:
<221> NAME/KEY: variation
<222> LOCATION: (4)..(8)
<223> OTHER INFORMATION: n may be A, T, G or C

<400> SEQUENCE: 19
ccannnnntg g                                                            11

<210> SEQ ID NO 20
<211> LENGTH: 11
<212> TYPE: DNA
<213> ORGANISM: Pseudomonas fluorescens
<220> FEATURE:
<221> NAME/KEY: variation
<222> LOCATION: (4)..(8)
<223> OTHER INFORMATION: n may be A, T, G or C

<400> SEQUENCE: 20
ccannnnntg g                                                            11

<210> SEQ ID NO 21
<211> LENGTH: 11
<212> TYPE: DNA
<213> ORGANISM: Methanobacterium wolfei
<220> FEATURE:
<221> NAME/KEY: variation
<222> LOCATION: (3)..(9)
<223> OTHER INFORMATION: n may be A, T, G or C

<400> SEQUENCE: 21
gcnnnnnnng c                                                            11

<210> SEQ ID NO 22
<211> LENGTH: 11
<212> TYPE: DNA
<213> ORGANISM: Methanobacterium wolfei
<220> FEATURE:
<221> NAME/KEY: variation
<222> LOCATION: (3)..(9)
<223> OTHER INFORMATION: n may be A, T, G or C

<400> SEQUENCE: 22
gcnnnnnnng c                                                            11

<210> SEQ ID NO 23
<211> LENGTH: 11
<212> TYPE: DNA
<213> ORGANISM: Bacillus sp.
<220> FEATURE:
<221> NAME/KEY: variation
<222> LOCATION: (3)..(9)
<223> OTHER INFORMATION: n may be A, T, G or C
```

```
<400> SEQUENCE: 23
ccnnnnnnng g                                                              11

<210> SEQ ID NO 24
<211> LENGTH: 11
<212> TYPE: DNA
<213> ORGANISM: Bacillus sp.
<220> FEATURE:
<221> NAME/KEY: variation
<222> LOCATION: (3)..(9)
<223> OTHER INFORMATION: may be A, T, G or C

<400> SEQUENCE: 24
ccnnnnnnng g                                                              11

<210> SEQ ID NO 25
<211> LENGTH: 11
<212> TYPE: DNA
<213> ORGANISM: Bacillus globigii
<220> FEATURE:
<221> NAME/KEY: variation
<222> LOCATION: (4)..(8)
<223> OTHER INFORMATION: n may be A, T, G or C

<400> SEQUENCE: 25
gccnnnnngg c                                                              11

<210> SEQ ID NO 26
<211> LENGTH: 11
<212> TYPE: DNA
<213> ORGANISM: Bacillus globigii
<220> FEATURE:
<221> NAME/KEY: variation
<222> LOCATION: (4)..(8)
<223> OTHER INFORMATION: may be A, T, G or C

<400> SEQUENCE: 26
gccnnnnngg c                                                              11
```